(12) United States Patent
Horito (10) Patent No.: US 11,033,229 B2
(45) Date of Patent: Jun. 15, 2021

(54) BABY FOOT STRAP

(71) Applicant: Rocketship, Inc., Provo, UT (US)

(72) Inventor: Michael Horito, Provo, UT (US)

( * ) Notice: Subject to any disclaimer, the term of this patent is extended or adjusted under 35 U.S.C. 154(b) by 544 days.

(21) Appl. No.: 14/750,977

(22) Filed: Jun. 25, 2015

(65) Prior Publication Data

US 2015/0374293 A1 Dec. 31, 2015

Related U.S. Application Data

(60) Provisional application No. 62/017,119, filed on Jun. 25, 2014.

(51) Int. Cl.
*A61B 5/00* (2006.01)
*A61B 5/1455* (2006.01)
*A61B 5/01* (2006.01)
*A61B 5/024* (2006.01)

(52) U.S. Cl.
CPC .......... *A61B 5/6829* (2013.01); *A61B 5/6831* (2013.01); *A61B 5/01* (2013.01); *A61B 5/02438* (2013.01); *A61B 5/14551* (2013.01); *A61B 2503/04* (2013.01); *A61B 2503/06* (2013.01); *A61B 2505/07* (2013.01); *A61B 2560/0242* (2013.01)

(58) Field of Classification Search
None
See application file for complete search history.

(56) References Cited

U.S. PATENT DOCUMENTS

| | | | | |
|---|---|---|---|---|
| 4,271,605 A | * | 6/1981 | Raczka | A61F 13/067 36/14 |
| 4,973,100 A | * | 11/1990 | Yang | B60J 11/00 150/166 |
| 6,671,532 B1 | * | 12/2003 | Fudge | A61B 5/14552 221/26 |
| 2003/0181799 A1 | * | 9/2003 | Lindekugel | A61B 5/14552 600/344 |
| 2004/0236298 A1 | * | 11/2004 | Coates | A61F 13/476 604/385.04 |
| 2011/0066061 A1 | * | 3/2011 | Colman | A61B 5/0836 600/532 |

FOREIGN PATENT DOCUMENTS

WO WO 2014035836 A1 * 3/2014 ......... G08B 21/0211

OTHER PUBLICATIONS

Covidien; Nellcor™ Preemie and Neonatal SpO2 Sensors, Nonadhesive; 2009.*

* cited by examiner

*Primary Examiner* — Kaylee R Wilson
*Assistant Examiner* — Jay B Shah
(74) *Attorney, Agent, or Firm* — Amy Fiene PC (57) ABSTRACT

A baby foot strap comprises a strap with an opening for a heel and a flange that wraps over the top of the foot, and at least one sensor attached to an interior of the strap, so as to monitor one or more desired health parameters of the baby.

10 Claims, 7 Drawing Sheets

Figure 13

US 11,033,229 B2

BABY FOOT STRAP

CROSS-REFERENCE TO RELATED APPLICATIONS

This application claims the benefit of and priority to U.S. Provisional Patent Application No. 62/017,119, filed Jun. 25, 2014, the entire contents of which are incorporated by reference herein.

BACKGROUND

A baby foot strap is a device that is often used to securely hold a monitor that detects signs of problems in an infant or toddler. In special care nurseries, infants and babies are continuously monitored to make sure they are healthy and breathing. One type of monitor routinely used in hospitals is a pulse oximeter, which includes a monitor that may be secured to a baby's foot with a baby foot strap. As light from the pulse oximeter travels through the skin, a sensor in the pulse oximeter measures the amount of hemoglobin that is carrying oxygen in the blood. Relying on a red light and a sensor to measure oxygen levels, it may be desirable to prevent surrounding light in the environment to interfere. Therefore, it may be beneficial to have proper support, securement, and contact of the monitor to the skin, provided by the baby foot strap.

Another use for baby foot straps is securing a monitor to a baby or toddler's foot in the home for parents wanting monitorization to prevent the onset of Sudden Infant Death Syndrome (SIDS), a leading cause of death among infants ages 1 month to 1 year old. Using baby foot straps can be problematic because many baby foot straps fail to account for growth and different foot sizes. This can prevent proper securement, making it easier for a baby or toddler to wriggle out of the baby foot strap, causing false alarms. Also, it can prevent proper measurements in general.

Other common problems with baby foot straps in the market include that they are bulky, making them uncomfortable. Babies and toddlers may find it difficult to position themselves or reposition themselves in bed. Also, baby foot straps are often air constrictive, making the skin difficult to air out, causing soreness and rashes.

SUMMARY

Another use for baby foot straps is securing a monitor to a baby or toddler's foot in the monitors to infants, babies, and toddlers and obtain information that can help signal warnings for signs of distress. A baby foot strap that is easily attached, cleaned, and that allows for growth is desirable. Therefore, a baby foot strap with an opening for the heel and a strap over the top of the foot is described.

In an embodiment of the present invention, a baby foot strap comprises a strap that includes a generally oblong opening for a heel and a first flange that wraps over at least a portion of an upper surface of a foot, the first flange removably joining two sides of the strap over the upper surface of the foot. The foot strap also includes at least one electronic device attached to the strap.

DETAILED DESCRIPTION

The following describes a baby foot strap that secures one or more monitors to a baby's foot. Monitors can track such things as vitals like heart rate, oxygen levels, temperature, and sleep habits, including a roll-over alert if the baby turns face down in a crib. This type of data may be directed to an app where parents, physicians, and other caregivers may check on a child's health relatively quickly. Monitors alluded to may include, for example, pulse oximeters, temperature monitors, moisture monitors, heart rate monitors, etc.

Figure 1:
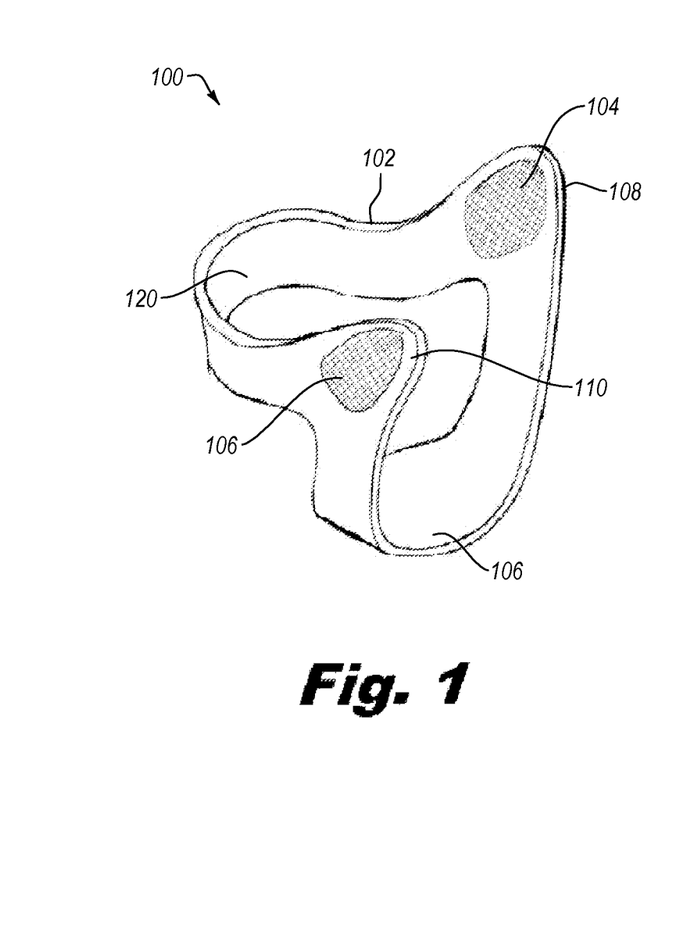
FIG. 1 shows a perspective view of a baby foot strap with multiple extended members used as straps.
Figure 2:
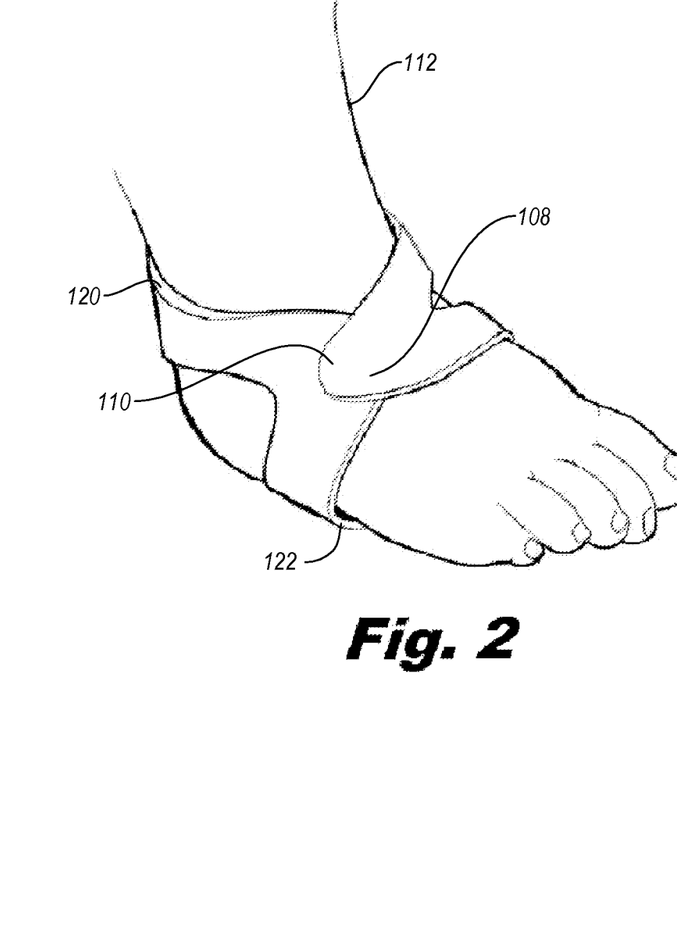
FIG. 2 shows a perspective view of a baby foot strap with multiple extended members used as straps being worn on a baby's foot.

Turning to FIGS. 1 and 2, a baby foot strap 100 is shown. The baby foot strap 100 may include a single strap 102 that forms a loop, or ring. In other words, the strap 102 curves around to rejoin itself at ends, forming a central opening that is generally oblong, for the heel. Two opposing sides 108 and 110 of the strap 102 may curve, extend, or jut upwards to make the opening extend around at least a portion of medial and lateral sides of a foot. The opposing sides 108 and 110 may form extended members, first and second flanges 108 and 110, with free ends. The thickness and width of the strap may be constant or may have variation, with thickness and width varying along the length of the strap, if desired.

The central opening may provide space for which a heel may be inserted. The strap 102 may be configured to lay on one or both of the medial and lateral sides of the ankle bone. In an embodiment, when worn, the location of the strap may be above or below one or both of the medial and lateral sides of the ankle bone.

Figure 3:
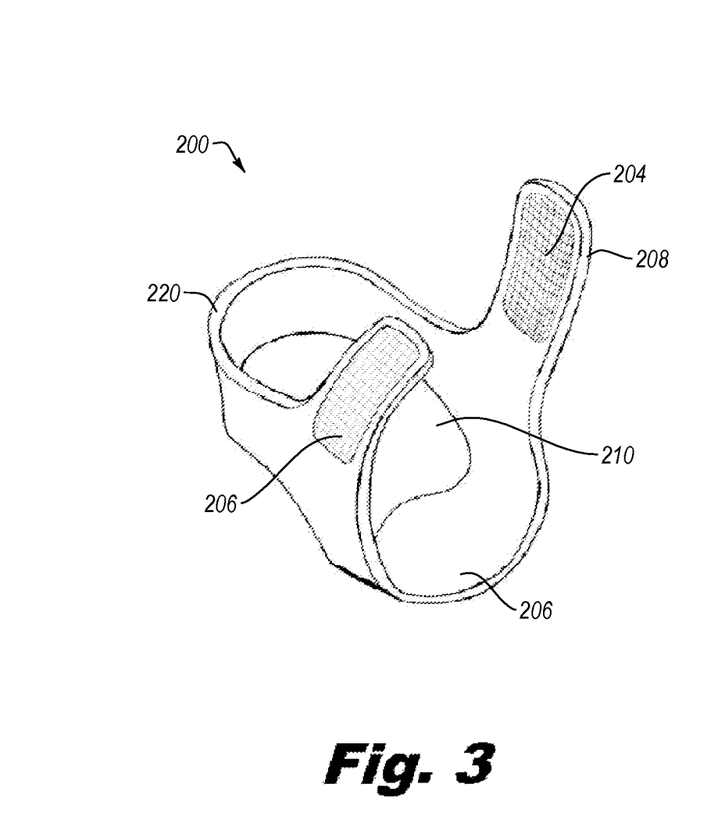
FIG. 3 shows a perspective view of a baby foot strap with extended members that form a single band over the top of the foot.

First and second flanges 108 and 110, located on either side of the strap 102, may be used to wrap the strap 102 around the foot. The first and second flanges 108 and 110 may be formed by the single strap 102, as formed by increasing width, or extended members that are an extension outward from the strap 102 on the sides of the strap 102. FIG. 3 shows an embodiment including increased extension relative to flanges 108 and 110 as compared to that of FIG. 1.

The central opening and the first and second flanges 108 and 110 may be configured to allow movement of the foot, including one or more of dorsiflexion, plantarflexion, inversion, eversion, pronation, and supination.

Referring to FIGS. 1 and 2, the first and second flanges 108 and 110 may be generally triangular extensions that originate from the sides and that curve over the top surface of the foot and overlap, or criss-cross, to be removably attached together. The triangular extensions may be a V-shape or pointed protuberance from the sides.

The first and second flanges 108 and 110 may include Velcro (hook and loop) 104 and 106, or other attachment means, to secure sides of the strap 102 to one another, over the foot. As shown, the first and second flanges 108 and 110 wrap around the top of the ankle. A back portion 120 of the strap 102 curves around the back and over of the ankle, or slightly above or slightly below the ankle. For example, it may be within 5 cm, 3 cm, 2 cm, or 1 cm of the back of the ankle, where positioned above or below. In an embodiment, the portion 120 may be somewhat higher in the back, and curve or angle downward as it approaches the ankle. A sole portion 122 wraps around the sole of the foot. The sole portion 122 may contact a central region of the sole of the foot. Alternatively, the sole portion 122 may contact a region that is more proximal to the ankle or more distal thereto, under the sole of the foot near a central region, around the ankle and over the top of the foot at a central region.

Configurations of the strap may be designed relative to bony surfaces and landmarks of the foot and lower limbs, such as the malleolus, calcaneus, metatarsals, talus, cuboid, cuneiform, tibia, fibula, as well as other features. For example, the strap in an embodiment may extend around any such feature, particularly if it protrudes, rather than covering it. Inherent in at least some embodiments is the advantage that the heel opening allows for growth of the heel and foot. The sides (e.g., 108 and 110) may be tightened and loosened during readjustment to allow for growth of the heel or foot.

Variations include that the strap have no central opening, or a limited central opening, thus providing a heel cup, which may cover all or a portion of the heel. Note that a heel cup may be formed by the strap or that the heel cup may be a separate member that is attached to the strap. If the heel cup is a separate member, it may comprise a separate strap-like member, or a plastic cup, or some other type of member that attaches the heel cup to the baby foot strap 100.

Figure 4:
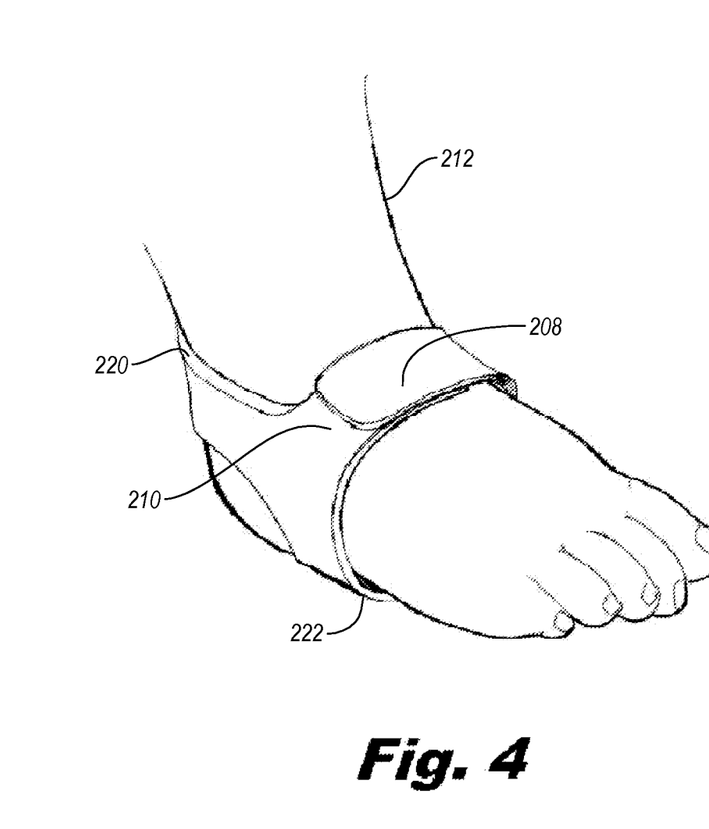
FIG. 4 shows a perspective view of a baby foot strap with extended members that form a single band over the top of the foot being worn on a baby's foot.

Turning to FIGS. 3 and 4, a baby foot strap 200 includes strap 202, first and second flanges 208 and 210, Velcro 204 and 206, back portion 220, and sole portion 222. The first and second flanges 208 and 210 may be elongate band-like, or strip-like extensions that extend generally perpendicularly upward from the sides and may have free ends that flexibly curve around over the upper surface of the foot 212, for attachment to one another. The first and second flanges 208 and 210 reach over the top of the foot and criss-cross, overlap, or join at free ends thereof, thus forming a releasable band over the top of the foot. Joinder may be enabled by means of Velcro or other means as described herein.

The width and thicknesses for the baby foot strap may vary. One of the advantages is that the baby foot strap may be relatively small, lightweight, easily transportable, easily worn, easily removed, and is non-bulky. Some sensors may be heavy and bulky, making it difficult for babies to move their feet and get comfortable. Furthermore, the straps may be tight enough such that sensors and lights contact the skin without light leakage and/or poor sensing contact, a problem that could negatively affect data readings. Also, the straps may be secured so that the baby cannot easily kick them off or slide them off their feet.

Figure 5:
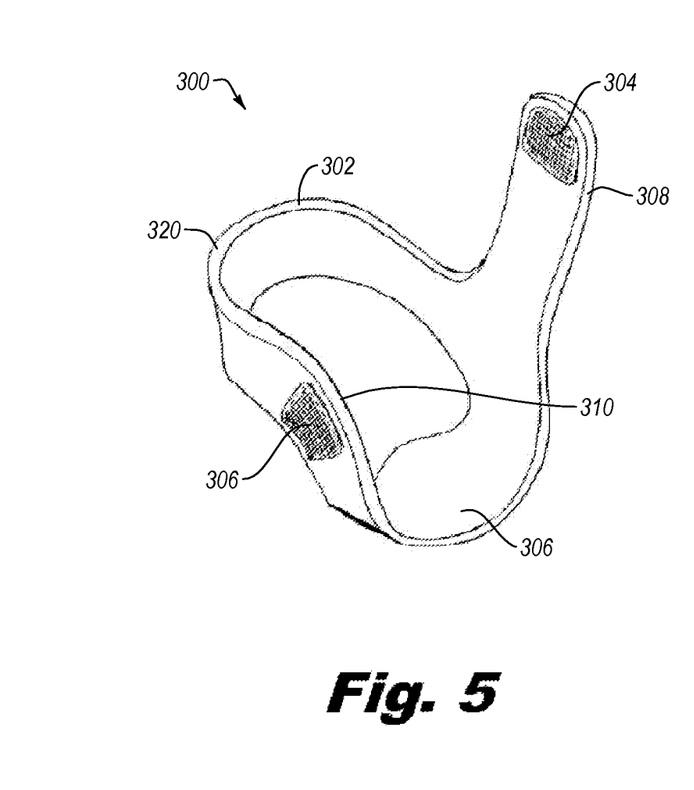
FIG. 5 shows a perspective view of a baby foot strap with a single extended member used as a strap.
Figure 6:
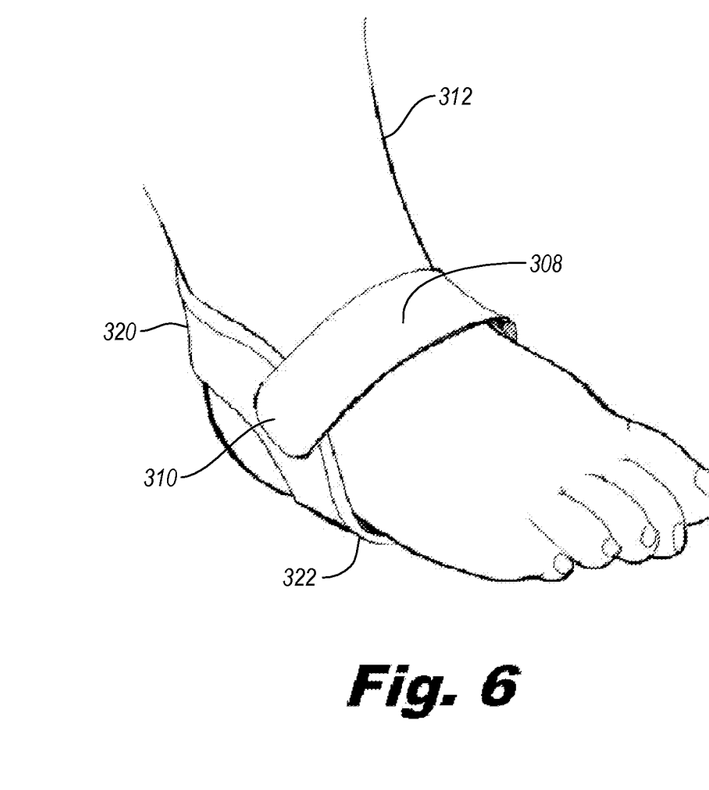
FIG. 6 shows a perspective view of a baby foot strap with a single extended member used as a strap being worn on a baby's foot.

Turning to FIGS. 5 and 6, a baby foot strap 300 is shown that includes one strap 302 that wraps over the top of the foot 312 and is secured to the other side 306 of the baby foot strap 300. Strap 300 is an example of an embodiment with an opening for a heel and an flange 308 that wraps over the top of the foot, where the flange 308 may be a separate piece from the rest of strap 302 (e.g., riveted, glued, or otherwise attached thereto). At least one sensor may be attached to an interior of the strap 302 and used for monitorization purposes. The sensor (e.g., an electronic sensing device) may be attached or provided anywhere on the strap (e.g., including on the sides, heel, top portion, sole, etc.).

Suitable materials for the baby foot strap may include, but are not limited to silicone, thermoplastic elastomer (TPE), plastic, elastic, elastomeric material, other materials, or any combination thereof. Securement may be obtained using snaps, Velcro, ties, buckles, and other securement means that are commonly known in the art.

Figure 7:
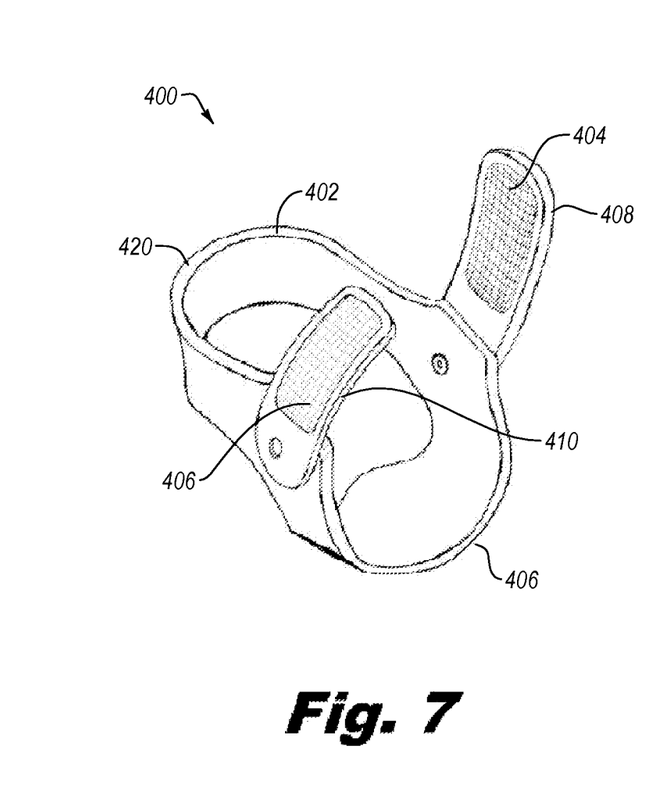
FIG. 7 shows a perspective view of a baby foot strap with two removable, pivotable straps.
Figure 8:
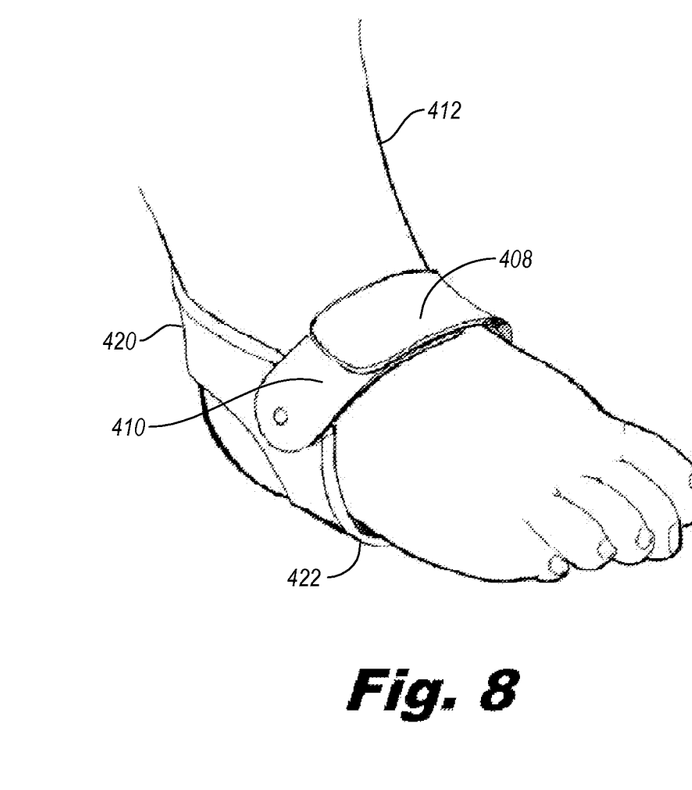
FIG. 8 shows a perspective view of a baby foot strap with two removable, pivotable straps being worn on a baby's foot.

Turning to FIGS. 7 and 8, two removable, pivotable flanges 408 and 410 are included with the baby foot strap 400. Note that more than one, two, or more than two flanges may be used. In an embodiment, the flanges may be removable (e.g., Velcro, etc.) from the remainder of the device, or may be non-removable relative to the baby foot strap, as desired.

The flanges 408, 410 as shown are pivotable as it is mounted to strap 400 with a rivet or similar mechanism, with the advantage that the flanges may be adjusted to conform to differently sized feet or adjustable to accommodate growing feet. If feet become swollen or change shape, the flanges may be wrapped higher or lower on the foot region. In addition, the flanges may be adjusted to be looser if the foot were swollen. Note, however, that some embodiments may include flanges that are not pivotally attached to the remainder of the strap (e.g., see FIGS. 1-6).

The flanges as shown wrap over the foot with one flange overlapping the other flange. Alternatively, the two flanges may lay flush with the skin, with ends connecting, e.g., end-to-end, instead of overlapping (e.g., through a buckling or similar mechanism). Any of the various described securement features described herein may be employed. As shown, Velcro may be particularly suitable, allowing some variation and easy adjustment in tightness.

Figure 9:
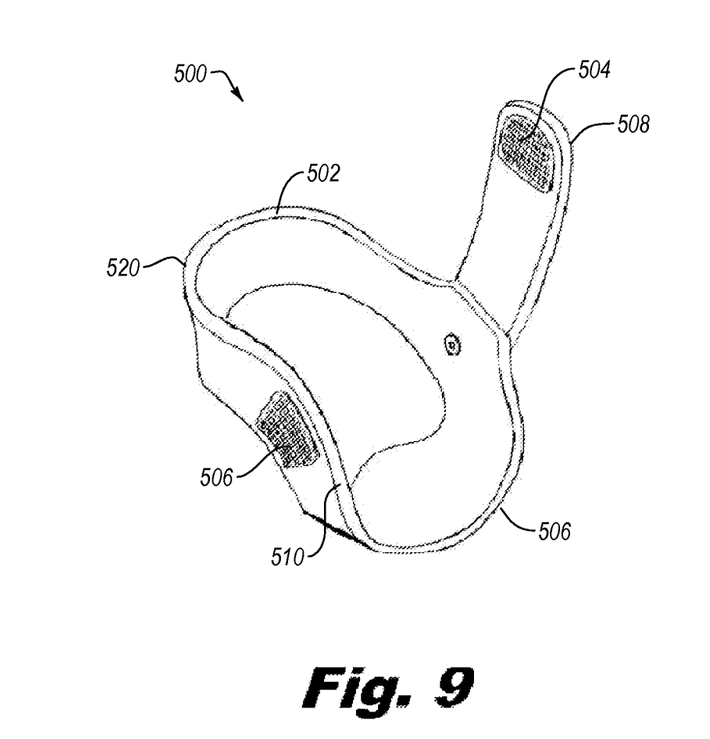
FIG. 9 shows a perspective view of a baby foot strap with a removable, pivotable strap.
Figure 10:
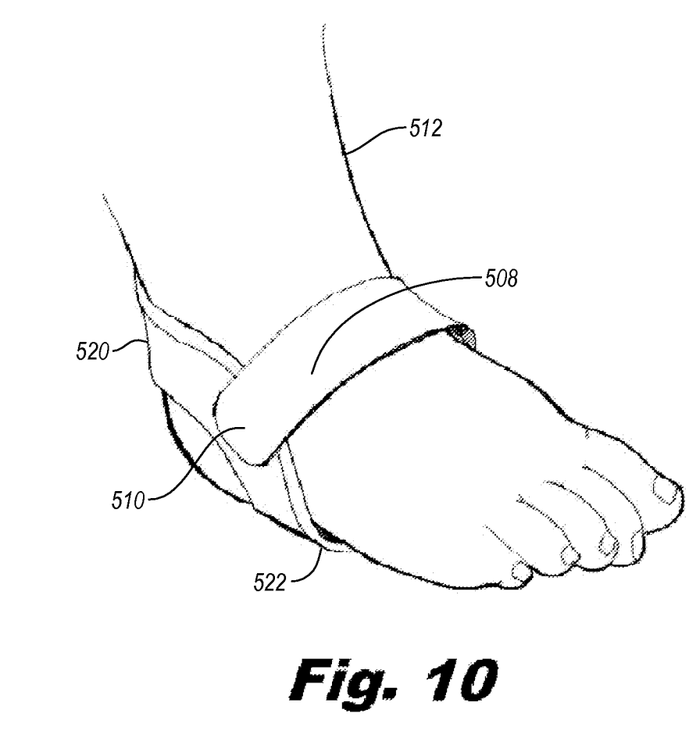
FIG. 10 shows a perspective view of a baby foot strap with a removable, pivotable strap being worn on a baby's foot.

Turning to FIGS. 9 and 10, a removable, pivotable flange 508 is shown as included with the baby foot strap 500. The removable flange 508 is advantageous because a baby's foot size grows rapidly, and replacing the baby foot strap 500 multiple times per year may become expensive. Rather than replacing the entire strap 500, a user may wish to obtain a relatively longer flange 508, remove the initially attached flange, and replace it with the longer flange to accommodate foot growth that has occurred. As shown, the flange 508 may pivot around the point of securement on strap 502 or relative to some other point. This is advantageous because it allows the baby foot strap 500 another avenue by which to obtain a better fit around the ankle and foot area, as mentioned previously. By having a more modular bootie (e.g., with replaceable and/or interchangeable flanges or other components) that can grow as the baby grows, the life of the baby foot strap is increased. Note that other contemplated embodiments may include non-pivoting flanges.

Figure 11:
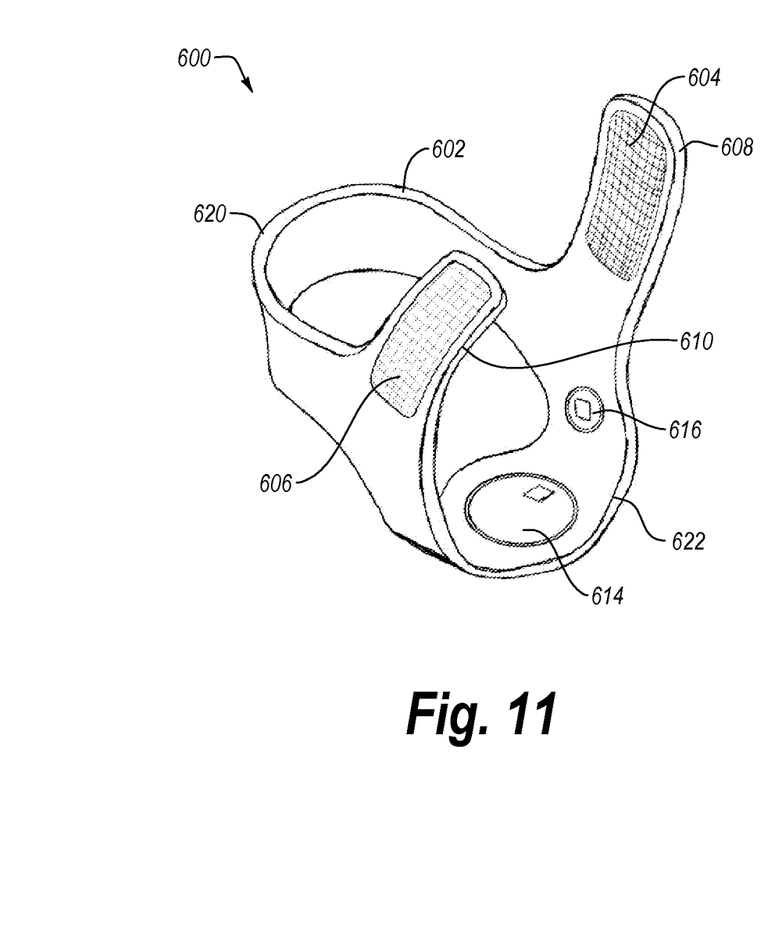
FIG. 11 shows a perspective view of a baby foot strap with a monitoring device attached.
Figure 12:
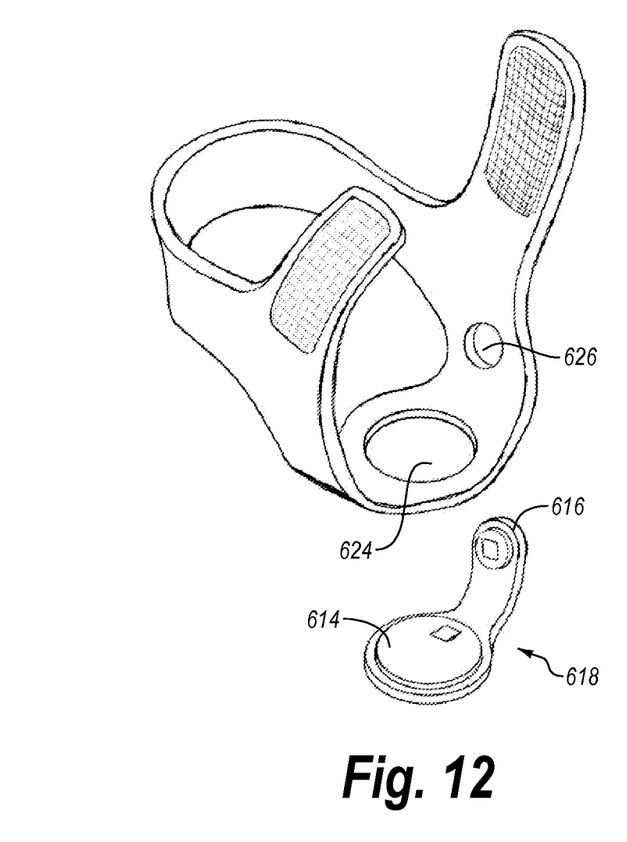
FIG. 12 shows a perspective view of a baby foot strap with a monitoring device unattached.

FIGS. 11 and 12 show a baby foot strap 600 including an electronic device 614 received within a hole 624 in the sole portion 622 of strap 602. In other embodiments, the device 618 or other sensor may be placed elsewhere (e.g., under a flange, or elsewhere on strap 602). Baby foot strap 600 similarly includes first and second flanges 608 and 610, with Velcro or another attachment mechanism 604 and 606. Baby foot strap 600 further shows a second hole 626 for receipt of another sensor or another electrode of the same device 618. One or more sensors, electrodes, etc. may be provided in the baby foot strap 600 for monitoring one or more desired parameters. For example, in an embodiment, device 618 may include two electrodes or sensors 614 and 616 for sensing one or more desired parameters. Sensor or portion 614 is shown received within hole 624, while sensor or portion 616 is shown received within hole 626. As shown, the outer edges of at least a portion of the sensor (e.g., 614 and 616) of electronic device 618 are removably attached along the outer edges of the respective hole (624 and 626). In an embodiment, the size of the received portion of the monitoring device may be such relative to the hole so as to create a friction fit, or snap fit of the device within the hole. In another embodiment, other attachment mechanisms may be employed (e.g., a snap, Velcro, adhesive, a set screw, etc.)

Figure 13:
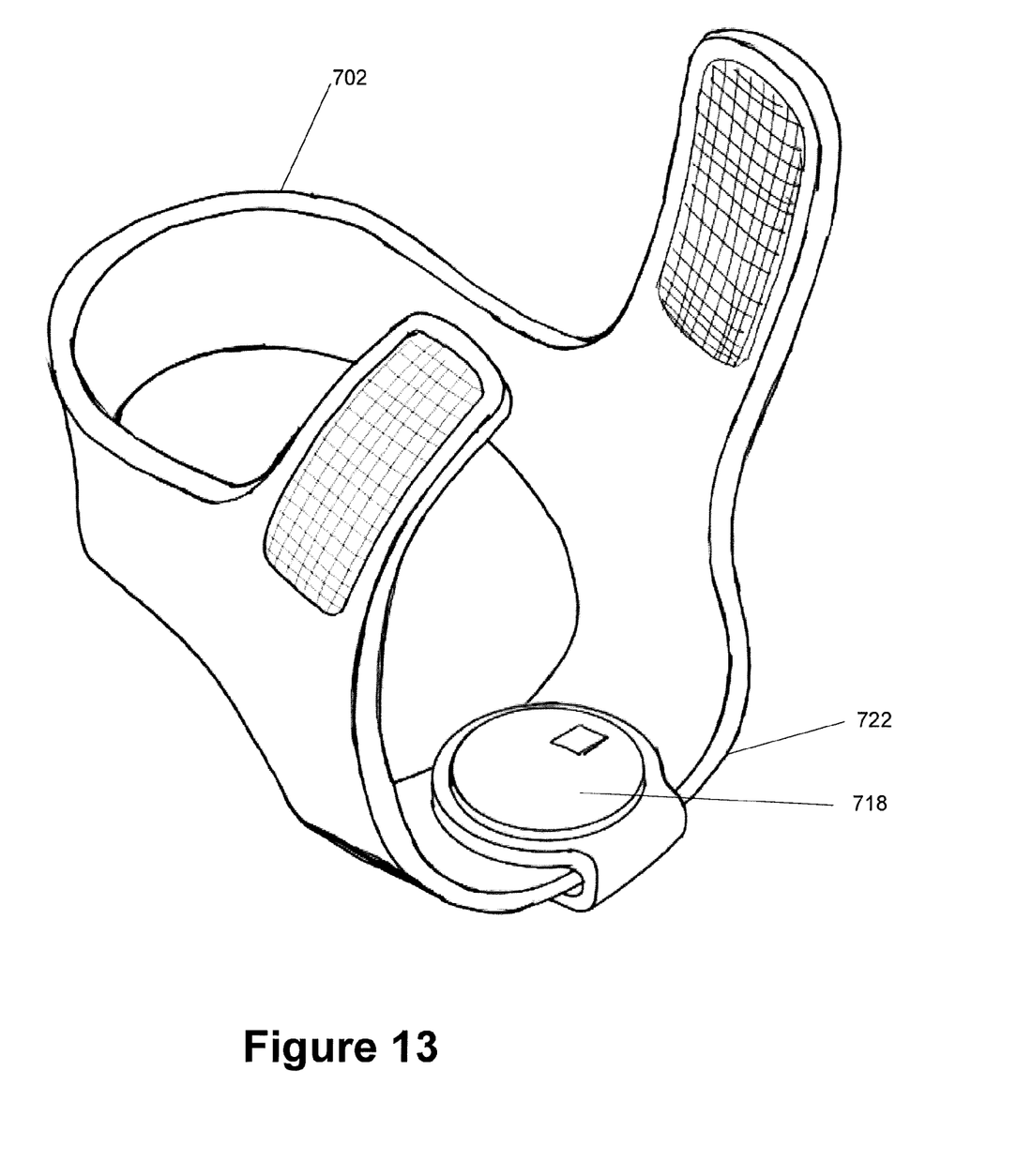
FIG. 13 shows a perspective view of a baby foot strap with a monitoring device attached.

FIG. 13 illustrates another configuration of a strap 702 for a baby foot strap in which the electronic device 718 is shown snapped or otherwise attached over the sole portion of the strap 702, rather than received within any hole formed in the strap 702. In another embodiment, a hole may be disposed in the sole portion 722 over which device 718 is disposed. For example, a snap on the underside of the device may be provided, so that the device flexibly wraps around portion 722, and snaps into itself through such a hole. Of course, other configurations are possible. The device 718 may be placed elsewhere on the baby foot strap device (e.g., elsewhere on strap 702, the flanges thereof, etc.

While reference has been made to certain specific embodiments and examples, it will be recognized by those skilled in the art that many variations are possible without departing from the scope and spirit of the description, and that the claims are intended to cover all changes and modifications of the embodiments which do not depart from the spirit of the description presented herein.

I claim:

1. A baby ankle device adapted to wrap around an ankle region of a foot, the baby ankle device consisting of:
   a strap that is single and contiguous, the strap defining an opening that is dimensioned for a heel of the foot to be inserted,
   a back portion of the strap adapted to extend from a back of the heel to sides of an ankle bone of the foot;
   two side portions of the strap that extend from opposite end portions of the back portion, the side portions of the strap having an inverted V-shape or U-shape adapted to bend or curve at or adjacent to the ankle bone toward an arch of the foot;
   a sole portion of the strap adapted to extend from ends of the two side portions of the strap across a bottom facing surface of the arch of the foot;
   a first and second flange of the strap adapted to extend from the two side portions of the strap across an upper facing surface over the arch of the foot, joinder of the two side portions of the strap by the first and second flange adapted to provide simultaneous attachment of the strap around the arch of the foot and the back of the heel while allowing a distal region of the arch of the foot to be free, the joinder defining both 1) a variable circumferential opening around the arch of the foot and 2) a variable circumferential opening from the heel to the top surface of the arch of the foot, and thereby anticipating growth of the foot and a lower leg attached to the foot; and
   at least one mounting hole extending therethrough in the sole portion of the strap; and
   at least one electronic sensor device disposed with a friction fit or snap fit within the mounting hole in the sole portion of the strap so as to contact a skin surface on the arch of the foot.

2. The baby foot device in claim 1, wherein joinder of the two side portions of the strap by the first and second flange includes one or more of hook and loop, buttons, snaps, buckles, or ties.

3. The baby ankle device in claim 1, wherein an end portion of the second flange overlaps an end portion of the first flange at a variable length and is removably joined.

4. The baby ankle device in claim 3, wherein the first and second flanges have triangular extensions from the two side portions of the strap.

5. The baby ankle device in claim 3, wherein the first and second flanges are elongate strips that extend perpendicularly upward from the two side portions of the strap and have free ends that flexibly curve around over the upper surface of the foot.

6. The baby ankle device in claim 3, wherein the first and second flanges are separate from one another and pivotably connected to the two side portions of the strap.

7. The baby ankle device in claim 1, wherein the first flange is separate from the strap and pivotably connected to one side of the strap.

8. The baby ankle device in claim 1, wherein the strap is made of one or more of silicone, thermoplastic elastomer (TPE), plastic, elastic, or elastomeric material.

9. A baby ankle device adapted to wrap around an ankle region of a foot, the baby ankle device consisting of:
   a back portion that is adapted to extend across a heel of the foot;
   a sole portion that is adapted to extend across an arch of the foot;
   two side portions adapted to extend from ends of the back portion to ends of the sole portion, the two side portions bending or curving in an inverted V-shape or U-shape from the ends of the back portion toward the ends of the sole portion;
   a first and second flange adapted to extend from the two side portions across a top of the foot over the arch of the foot and thereby simultaneously join the two side portions around the heel and the arch of the foot;
   at least one oblong opening defined by the back portion, the sole portion, and the two side portions for the heel to be inserted;
   a hole extending therethrough in the sole portion, the sole portion dimensioned to receive and removably secure an electronic sensor device within the hole; and
   at least one electronic sensor device disposed within the hole to contact a skin surface along the arch of the foot, the at least one electronic sensor device to be flexibly wrapped around the sole portion to attach to itself through the hole for securement to the sole portion.

10. A baby ankle device adapted to wrap around an ankle region of a foot, the baby ankle device consisting of:
    a back portion that is adapted to extend across a heel of the foot;
    a sole portion that is adapted to extend across an arch of the foot;

two side portions adapted to extend from ends of the back portion to ends of the sole portion, the two side portions bending or curving in an inverted V-shape or U-shape from the ends of the back portion toward the ends of the sole portion over the ankle region;

a first and second flange adapted to extend from a mid-section of the two side portions across a top of the foot over the arch of the foot, end portions of the first and second flange to be removably joined and thus simultaneously join the two side portions around the heel and the arch of the foot, the end portions joined at a variable position to create a variable fit that encompasses the heel, the arch, and the top facing surface of the foot over the arch;

at least one oblong opening defined by the back portion, the sole portion, and the two side portions for the heel to be inserted;

a hole extending therethrough from one side of the sole portion to an opposing side of the sole portion, the sole portion dimensioned to receive and removably secure an electronic sensor device within the hole; and at least one electronic sensor device disposed within the hole with a friction fit or snap fit so as to contact a skin surface on the arch of the foot.

* * * * *